United States Patent [19]

Beck et al.

[11] 4,065,463
[45] Dec. 27, 1977

[54] HERBICIDAL 2-METHYL-4-PHENYL-5-ISOXAZOLI-NONES

[75] Inventors: James Richard Beck; Robert Peter Gajewski, both of Indianapolis, Ind.

[73] Assignee: Eli Lilly and Company, Indianapolis, Ind.

[21] Appl. No.: 726,726

[22] Filed: Sept. 27, 1976

Related U.S. Application Data

[63] Continuation-in-part of Ser. No. 639,749, Dec. 11, 1975, Pat. No. 4,000,155.

[51] Int. Cl.$^2$ ............................................. C07D 261/12
[52] U.S. Cl. .................................... 260/307 A; 71/88; 560/38

[58] Field of Search ..................................... 260/307 A

[56] References Cited

PUBLICATIONS

De Sarlo et al.-"Tetrahedron" -1966-vol. 22, pp. 2989-2992.

*Primary Examiner*—Raymond V. Rush
*Attorney, Agent, or Firm*—William E. Maycock; Arthur R. Whale

[57] ABSTRACT

A small class of 2-methyl-4-phenyl-5-isoxazolinones are herbicides. The phenyl ring is substituted in the meta position. The compounds are particularly useful as pre-emergence herbicides.

1 Claim, No Drawings

HERBICIDAL 2-METHYL-4-PHENYL-5-ISOXAZOLINONES

CROSS REFERENCE

This application is a continuation-in-part of our copending application Ser. No. 639,749, filed Dec. 11, 1975, now U.S. Pat. No. 4,000,155.

BACKGROUND OF THE INVENTION

This invention belongs to the field of agricultural chemistry, and provides new herbicides. The growth of weeds, which are plants growing where they are not wanted, has inevitable deleterious effects on crops which are infested with the weeds. Weeds growing in cropland, as well as in fallow land, consume soil nutrient and water, and compete with crop plants for sunlight. Thus, weed plants constitute a drain on the soil and cause measurable losses in yields.

The compounds of this invention are new to organic chemistry. Earlier workers have found herbicides among the pyridazinones, for example, U.S. Pat. No. 3,644,355. Pyrimidine herbicides have also been disclosed, such as the 3-phenyl-4-pyrimidinones of U.S. Pat. No. 3,823,135. The chemical literature shows some diphenyl-5-pyrazolinones, such as the 3-methyl- 1,4-diphenyl compound of Beckh, Ber. 31, 3164 (1898) and the 2-methyl-1,3-diphenyl compound of Knorr et al., Ber. 20, 2549 (1887). Antipyrine, a pharmaceutical pyrazolinone, is 2,3-dimethyl-1-phenyl-3-pyrazolin-5-one. Merck Index, 93 (8th Ed. 1968). DeSarlo et al. taught 2-methyl-4-phenyl-3-isoxazolin-5-ones in Tetrahedron 22, 2989-94 (1966).

SUMMARY OF THE INVENTION

This invention provides new herbicidal compounds of the formula

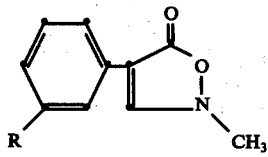

wherein R represents chloro or trifluoromethyl.

DESCRIPTION OF THE PREFERRED EMBODIMENT

The compounds of this invention are made most advantageously by the following process. First, a methyl or ethyl ester of a substituted phenylacetic acid is reacted with di(Alk)formamide di(Alk) acetal, neat or in dimethyl-formamide, to produce an intermediate substituted ester of atropic acid of the formula (I) below.

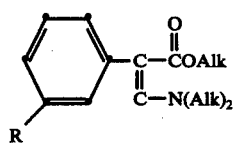

The term Alk refers to methyl or ethyl. The reaction is carried out at temperatures from about 80° to about 140° C. in a flask open to the atmosphere.

The intermediate I is then reacted with methylhydroxylamine to form the isoxazolinones. The reagent may be used as the free base or hydrohalides. When methylhydroxylamine free base is used, the reaction is carried out in an aprotic solvent. The aromatic solvents such as benzene and toluene, the aliphatics such as hexane and octane, and the halogenated solvents such as methylene chloride and chloroform are appropriate solvents. The most convenient reaction temperature is the reflux temperature of the reaction mixture, but other temperatures from room temperature to about 120° C. can be used if convenient in a given instance.

When a methylhydroxylamine hydrohalide is used, the reaction can be carried out in an aprotic solvent as described above, in the presence of a base. Tertiary organic amines such as triethylamine, pyridine, triethanolamine and the like, and inorganic bases such as potassium carbonate, sodium bicarbonate, alkali metal hydroxides and the like are satisfactory bases. Alternatively, the reaction may be carried out in a lower alkanol. The same temperatures are used as in the reactions with free bases.

All of the starting compounds used in synthesizing the compounds are commonly known in the chemical art and are readily obtainable.

A few typical preparative examples will be shown to assure that organic chemists can obtain any desired compound of this invention. The products described below were identified by nuclear magnetic resonance analysis and elemental microanalysis.

EXAMPLE 1

2-methyl-4-(α,α,α-trifluoro-m-tolyl)-3-isoxazolin-5-one

A 10.9 g. portion of 3-trifluoromethylphenylacetic acid, methyl ester, was combined with 11.9 g. of dimethylformamide dimethyl acetal and the mixture was heated overnight on the steam bath. In the morning, the reaction mixture was taken up in methanol and poured over ice. The aqueous mixture was filtered, and the solids were recrystallized from aqueous ethanol to produce 4 g. of m-trifluoromethyl-β-(dimethylamino)atropic acid, methyl ester, m.p. 45°-49° C.

A 2.7 g. portion of the above intermediate was mixed with 0.84 g. of methylhydroxylamine hydrochloride and 1 g. of triethylamine in 50 ml. of benzene. After the mixture was stirred at reflux temperature overnight, it was evaporated to dryness, and the residue was taken up in water. The undissolved solids were separated by filtration, air-dried and recrystallized from ethyl acetate-hexane to produce 1.3 g. of 2-methyl-4-(α,α,α-trifluoro-m-tolyl)-3-isoxazolin-5-one, m.p. 132°-134° C.

|   | Theoretical | Found |
|---|---|---|
| C | 54.33% | 54.05% |
| H | 3.32 | 3.25 |
| N | 5.76 | 5.77 |

EXAMPLE 2

2-methyl-4-(3-chlorophenyl)-3-isoxazolin-5-one

A 1.75 g. portion of m-chloro-β-(dimethylamino)-atropic acid, methyl ester, was prepared according to the first step of Example 1, and was combined with 0.67 g. of methylhydroxylamine hydrochloride in 50 ml. of methanol. The mixture was refluxed for 72 hours, and was then evaporated to dryness under vacuum. The residue was partitioned between water and ethyl acetate, and the organic layer was dried over sodium sulfate and evaporated to dryness under vacuum. The product was recrystallized from cyclohexane-ethyl acetate to produce 1.15 g. of 2-methyl-4-(3-chlorophenyl)-3-isoxazolin-5-one, m.p. 131° C.

|   | Theoretical | Found |
|---|---|---|
| C | 57.28% | 57.41% |
| H | 3.82 | 3.81 |
| N | 6.68 | 6.83 |

The compounds of this invention have been tested against a variety of crop and weed species to determine their efficacy in agriculture. For example, the compound of Example 1, when applied preemergence at the rate of 9.0 kilograms per hectare, produced only slight injury to corn while severely injuring large crabgrass and producing moderate injury to pigweed and foxtail.

Since the compounds of this invention are herbicidally effective when applied preemergence, they are used by applying the compounds to the soil, where they come into contact with germinating and emerging weeds.

As agricultural chemists will appreciate, the best application rate of a given compound of the invention for the control of a given weed varies depending upon the climate, soil texture, water and organic matter contents of the soil, and other factors known to those skilled in plant science. It will be found, however, that the optimum application rate is usually in the range from about 1 to about 20 kg./ha.

The compounds are applied to the soil in the manners usual in agriculture. It is best to apply the compounds in the form of the herbicidal compositions which are important embodiments of the present invention. They may be applied to the soil in the form of either water-dispersed or granular compositions, the preparation of which will be discussed below. Usually, water-dispersed compositions will be used for the application of the compounds to emerged weeds. The compositions are applied with any of the many types of sprayers and granular applicators which are in wide use for the distribution of agricultural chemicals over soil or standing vegetation. In general, the compositions are formulated in the manners usual in agricultural chemistry.

Very often, the compounds are formulated as concentrated compositions which are applied to the soil in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier, and surfactants. The concentration of the compound is usually from about 10 percent to about 90 percent. The inert carrier is usually chosen from among the attapulgite clays, the montmorillonite clays, the kaolin clays, the diatomaceous earths and the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carriers, which is then dried and coarsely ground to produce the desired granular product.

We claim:
1. The compound 2-methyl-4-($\alpha,\alpha,\alpha$-trifluoro-m-tolyl)-3-isoxazolin-5-one.

* * * * *